(12) United States Patent
Grey

(10) Patent No.: US 7,531,675 B1
(45) Date of Patent: May 12, 2009

(54) DIRECT EPOXIDATION PROCESS USING IMPROVED CATALYST COMPOSITION

(75) Inventor: Roger A. Grey, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 11/977,360

(22) Filed: Oct. 24, 2007

(51) Int. Cl.
*C07D 301/06* (2006.01)

(52) U.S. Cl. .................. 549/533; 502/74; 502/242; 549/531

(58) Field of Classification Search .......... 549/533; 502/66, 311, 326, 349, 74, 242
See application file for complete search history.

(56) References Cited

U.S. PATENT DOCUMENTS

| | | | |
|---|---|---|---|
| 3,351,635 A | 11/1967 | Kollar | |
| 4,367,342 A | 1/1983 | Wulff et al. | |
| 4,410,501 A | 10/1983 | Taramasso et al. | |
| 4,666,692 A | 5/1987 | Taramasso et al. | |
| 4,833,260 A | 5/1989 | Neri et al. | |
| 4,859,785 A | 8/1989 | Bellussi et al. | |
| 4,937,216 A | 6/1990 | Clerici et al. | |
| 6,005,123 A | 12/1999 | Dessau et al. | |
| 6,008,388 A | 12/1999 | Dessau et al. | |
| 6,399,794 B1 | 6/2002 | Hancu | |
| 6,498,259 B1 | 12/2002 | Grey et al. | |
| 7,026,492 B1 | 4/2006 | Kaminsky | |

FOREIGN PATENT DOCUMENTS

| | | |
|---|---|---|
| BE | 1001038 A7 | 6/1989 |
| JP | 4-352771 | 12/1992 |
| WO | WO 98/00413 | 1/1998 |

*Primary Examiner*—Bernard Dentz
*Assistant Examiner*—David E Gallis
(74) *Attorney, Agent, or Firm*—Kevin M. Carroll

(57) ABSTRACT

Catalysts useful for the direct epoxidation of olefins are disclosed. The catalysts comprise a noble metal, lead, bismuth, and a titanium or vanadium zeolite. The noble metal, lead, and bismuth may be supported on the titanium or vanadium zeolite. The catalyst may also be a mixture comprising the titanium or vanadium zeolite and a supported catalyst comprising the noble metal, lead, bismuth, and a carrier. The invention includes a process for producing an epoxide comprising reacting an olefin, hydrogen and oxygen in the presence of the catalyst. The process results in significantly reduced alkane byproduct formed by the hydrogenation of olefin.

11 Claims, No Drawings

DIRECT EPOXIDATION PROCESS USING IMPROVED CATALYST COMPOSITION

FIELD OF THE INVENTION

This invention relates to a catalyst and its use in the production of epoxides from hydrogen, oxygen, and olefins.

BACKGROUND OF THE INVENTION

Many different methods for the preparation of epoxides have been developed. Generally, epoxides are formed by the reaction of an olefin with an oxidizing agent in the presence of a catalyst. Ethylene oxide is commercially produced by the reaction of ethylene with oxygen over a silver catalyst. Propylene oxide is commercially produced by reacting propylene with an organic hydroperoxide oxidizing agent, such as ethylbenzene hydroperoxide or tert-butyl hydroperoxide. This process is performed in the presence of a solubilized molybdenum catalyst, see U.S. Pat. No. 3,351,635, or a heterogeneous titania on silica catalyst, see U.S. Pat. No. 4,367,342.

Besides oxygen and alkyl hydroperoxides, hydrogen peroxide is also a useful oxidizing agent for epoxide formation. U.S. Pat. Nos. 4,833,260, 4,859,785, and 4,937,216, for example, disclose olefin epoxidation with hydrogen peroxide in the presence of a titanium silicate catalyst.

Much current research is conducted in the direct epoxidation of olefins with oxygen and hydrogen. In this process, it is believed that oxygen and hydrogen react in situ to form an oxidizing agent. Many different catalysts have been proposed for use in the direct epoxidation process. Typically, the catalyst comprises a noble metal and a titanosilicate. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form a hydrogen peroxide in situ oxidizing agent. U.S. Pat. No. 6,498,259 describes a catalyst mixture of a titanium zeolite and a supported palladium complex, where palladium is supported on carbon, silica, silica-alumina, titania, zirconia, and niobia. Other direct epoxidation catalyst examples include gold supported on titanosilicates, see for example PCT Intl. Appl. WO 98/00413.

One disadvantage of the described direct epoxidation catalysts is that they are prone to produce non-selective byproducts such as glycols or glycol ethers formed by the ring-opening of the epoxide product or alkane byproduct formed by the hydrogenation of olefin. U.S. Pat. No. 6,008,388 teaches that the selectivity for the direct olefin epoxidation process is enhanced by the addition of a nitrogen compound such as ammonium hydroxide to the reaction mixture. U.S. Pat. No. 6,399,794 teaches the use of ammonium bicarbonate modifiers to decrease the production of ring-opened byproducts. U.S. Pat. No. 6,005,123 teaches the use of phosphorus, sulfur, selenium or arsenic modifiers such as triphenylphosphine or benzothiophene to decrease the production of propane. U.S. Pat. No. 7,026,492 discloses that the presence of carbon monoxide, methylacetylene, and/or propadiene modifier gives significantly reduced alkane byproduct. In addition, co-pending U.S. patent application Ser. No. 11/489,086 discloses that the use of a lead-modified palladium-containing titanium or vanadium zeolite reduces alkane byproduct formation.

As with any chemical process, it is desirable to attain still further improvements in the epoxidation methods and catalysts. We have discovered a new catalyst and its use in olefin epoxidation.

SUMMARY OF THE INVENTION

The invention is a catalyst comprising a noble metal, lead, bismuth, and a titanium or vanadium zeolite. In one embodiment, the catalyst is a mixture comprising a titanium or vanadium zeolite and a supported catalyst comprising a noble metal, lead, bismuth, and a carrier. The catalyst is useful in olefin epoxidation. Thus, the invention also includes an olefin epoxidation process that comprises reacting olefin, oxygen, and hydrogen in the presence of a catalyst comprising a titanium or vanadium zeolite, a noble metal, lead, and bismuth. This process surprisingly gives significantly reduced alkane byproduct formed by the hydrogenation of olefin compared to the process using catalyst systems that do not contain bismuth and lead.

DETAILED DESCRIPTION OF THE INVENTION

The catalyst of the invention comprises a titanium or vanadium zeolite, a noble metal, lead, and bismuth. Titanium or vanadium zeolites comprise the class of zeolitic substances wherein titanium or vanadium atoms are substituted for a portion of the silicon atoms in the lattice framework of a molecular sieve. Such substances, and their production, are well known in the art. See for example, U.S. Pat. Nos. 4,410,501 and 4,666,692.

Suitable titanium or vanadium zeolites are those crystalline materials having a porous molecular sieve structure with titanium or vanadium atoms substituted in the framework. The choice of titanium or vanadium zeolite employed will depend upon a number of factors, including the size and shape of the olefin to be epoxidized. For example, it is preferred to use a relatively small pore titanium or vanadium zeolite such as a titanium silicalite if the olefin is a lower aliphatic olefin such as ethylene, propylene, or 1-butene. Where the olefin is propylene, the use of a TS-1 titanium silicalite is especially advantageous. For a bulky olefin such as cyclohexene, a larger pore titanium or vanadium zeolite such as a zeolite having a structure isomorphous with zeolite beta may be preferred.

Particularly preferred titanium or vanadium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), "TS-3" (as described in Belgian Pat. No. 1,001,038), and Ti-MWW (having an MEL topology analogous to that of the MWW aluminosilicate zeolites). Titanium-containing molecular sieves having framework structures isomorphous to zeolite beta, mordenite, ZSM-48, ZSM-12, SBA-15, TUD, HMS, and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

Preferred titanium zeolites will generally have a composition corresponding to the following empirical formula $xTiO_2 (1-x)SiO_2$ where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

In one embodiment of the invention, the noble metal, bismuth and lead are supported on the titanium or vanadium zeolite. In another embodiment of the invention, the noble metal, bismuth and lead are supported on a carrier to form a supported catalyst which is then mixed with the titanium or vanadium zeolite.

Thus, the catalyst of the invention optionally comprises a carrier. The carrier is preferably a porous material. Carriers are well-known in the art. For instance, the carrier can be inorganic oxides, clays, carbon, and organic polymer resins. Preferred inorganic oxides include oxides of Group 2, 3, 4, 5, 6, 13, or 14 elements. Particularly preferred inorganic oxide carriers include silica, alumina, silica-aluminas, titania, zirconia, niobium oxides, tantalum oxides, molybdenum oxides, tungsten oxides, amorphous titania-silica, amorphous zirconia-silica, amorphous niobia-silica, and the like. The carrier may be a zeolite, but is not a titanium or vanadium zeolite. Preferred organic polymer resins include polystyrene, styrene-divinylbenzene copolymers, crosslinked polyethyleneimines, and polybenzimidizole. Suitable carriers also include organic polymer resins grafted onto inorganic oxide carriers, such as polyethylenimine-silica. Preferred carriers also include carbon. Particularly preferred carriers include carbon, silica, silica-aluminas, zirconia, niobia, and titania (in particular anatase titanium dioxide).

Preferably, the carrier has a surface area in the range of about 1 to about 700 m$^2$/g, most preferably from about 10 to about 500 m$^2$/g. Preferably, the pore volume of the carrier is in the range of about 0.1 to about 4.0 mL/g, more preferably from about 0.5 to about 3.5 mL/g, and most preferably from about 0.8 to about 3.0 mL/g. Preferably, the average particle size of the carrier is in the range of about 0.1 to about 500 µm, more preferably from about 1 to about 200 µm, and most preferably from about 10 to about 100 µm. The average pore diameter is typically in the range of about 10 to about 1000 Å, preferably about 20 to about 500 Å, and most preferably about 50 to about 350 Å.

The catalyst of the invention also comprises a noble metal, lead, and bismuth. The noble metal, lead, and bismuth may be added to the catalyst in any of a variety of ways, including: (1) noble metal, lead, and bismuth may be supported on the titanium or vanadium zeolite; and (2) noble metal, lead, and bismuth may be supported on the carrier to form a supported catalyst, which is then mixed with titanium or vanadium zeolite to form the catalyst.

While any of the noble metals can be utilized (i.e., gold, silver, platinum, palladium, iridium, ruthenium, osmium), either alone or in combination, palladium, platinum, gold, a palladium/platinum, or a palladium/gold combination are particularly desirable. Palladium is most preferred. The typical amount of noble metal present in the catalyst will be in the range of from about 0.01 to 10 weight percent, preferably 0.01 to 4 weight percent. There are no particular restrictions regarding the choice of noble metal compound used as the source of the noble metal. For example, suitable compounds include the nitrates, sulfates, halides (e.g., chlorides, bromides), carboxylates (e.g. acetate), oxides, and amine complexes of the noble metal.

Similarly, the oxidation state of the noble metal is not considered critical. The noble metal may be in an oxidation state anywhere from 0 to +4 or any combination of such oxidation states. To achieve the desired oxidation state or combination of oxidation states, the noble metal compound may be fully or partially pre-reduced after addition to the catalyst. Satisfactory catalytic performance can, however, be attained without any pre-reduction. To achieve the active state of the noble metal, the catalyst may undergo pretreatment such as thermal treatment in nitrogen, vacuum, hydrogen, or air.

The catalyst of the invention also contains lead. The typical amount of lead present in the catalyst will be in the range of from about 0.01 to 10 weight percent, preferably 0.01 to 5 weight percent. Preferably, the weight ratio of noble metal to lead in the catalyst is in the range of 0.1 to 10. While the choice of lead compound used as the lead source in the catalyst is not critical, suitable compounds include lead carboxylates (e.g., acetate), halides (e.g., chlorides, bromides, iodides), nitrates, cyanides, oxides, and sulfides.

The catalyst of the invention also contains bismuth. The typical amount of bismuth present in the catalyst will be in the range of from about 0.001 to 5 weight percent, preferably 0.01 to 2 weight percent. Preferably, the weight ratio of noble metal to bismuth in the catalyst is in the range of 0.1 to 10. While the choice of bismuth compound used as the bismuth source in the catalyst is not critical, suitable compounds include bismuth carboxylates (e.g., acetate, citrate), halides (e.g., chlorides, bromides, iodides), oxyhalides (e.g., oxychloride), carbonates, nitrates, phosphates, oxides, and sulfides.

Any suitable method may be used for the incorporation of the noble metal, lead, and bismuth into the catalyst. For example, the noble metal, lead, and bismuth may be supported on the zeolite or the carrier by impregnation, ion-exchange, or incipient wetness techniques. For example, the noble metal may be supported on the zeolite or the carrier by impregnation or by ion-exchange with, for example, palladium tetraammine chloride. If the lead, bismuth, and noble metal are added to the titanium or vanadium zeolite (or are added to the carrier), the order of addition is not considered critical. However, it is preferred to add the lead and bismuth compounds at the same time that the noble metal is introduced.

After noble metal, lead, and bismuth incorporation, the catalyst is isolated. Suitable catalyst isolation methods include filtration and washing, rotary evaporation and the like. The catalyst is typically dried prior to use in epoxidation. The drying temperature is preferably from about 50° C. to about 200° C. The catalyst may additionally comprise a binder or the like and may be molded, spray dried, shaped or extruded into any desired form prior to use in epoxidation.

After catalyst formation, the catalyst may be optionally thermally treated in a gas such as nitrogen, helium, vacuum, hydrogen, oxygen, air, or the like. The thermal treatment temperature is typically from about 20° C. to about 800° C. It is preferred to thermally treat the catalyst in the presence of an oxygen-containing gas at a temperature from about 200° C. to 700° C., and optionally reduce the catalyst in the presence of a hydrogen-containing gas at a temperature from about 20° C. to 600° C.

The epoxidation process of the invention comprises contacting an olefin, oxygen, and hydrogen in the presence of the catalyst. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$-$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

Oxygen and hydrogen are also required for the epoxidation process. Although any sources of oxygen and hydrogen are suitable, molecular oxygen and molecular hydrogen are preferred.

Epoxidation according to the invention is carried out at a temperature effective to achieve the desired olefin epoxidation, preferably at temperatures in the range of 0-250° C., more preferably, 20-100° C. The molar ratio of hydrogen to oxygen can usually be varied in the range of $H_2:O_2=1:10$ to 5:1 and is especially favorable at 1:5 to 2:1. The molar ratio of oxygen to olefin is usually 2:1 to 1:20, and preferably 1:1 to 1:10. A carrier gas may also be used in the epoxidation process. As the carrier gas, any desired inert gas can be used. The molar ratio of olefin to carrier gas is then usually in the range of 100:1 to 1:10 and especially 20:1 to 1:10.

As the inert gas carrier, noble gases such as helium, neon, and argon are suitable in addition to nitrogen and carbon dioxide. Saturated hydrocarbons with 1-8, especially 1-6, and preferably with 1-4 carbon atoms, e.g., methane, ethane, propane, and n-butane, are also suitable. Nitrogen and saturated $C_1$-$C_4$ hydrocarbons are the preferred inert carrier gases. Mixtures of the listed inert carrier gases can also be used.

Specifically in the epoxidation of propylene, propane or methane can be supplied in such a way that, in the presence of an appropriate excess of carrier gas, the explosive limits of mixtures of propylene, propane (methane), hydrogen, and oxygen are safely avoided and thus no explosive mixture can form in the reactor or in the feed and discharge lines.

The amount of catalyst used may be determined on the basis of the molar ratio of the titanium contained in the titanium zeolite to the olefin that is supplied per unit time. Typically, sufficient catalyst is present to provide a titanium/olefin per hour molar feed ratio of from 0.0001 to 0.1.

Depending on the olefin to be reacted, the epoxidation according to the invention can be carried out in the liquid phase, the gas phase, or in the supercritical phase. When a liquid reaction medium is used, the catalyst is preferably in the form of a suspension or fixed-bed. The process may be performed using a continuous flow, semi-batch or batch mode of operation.

If epoxidation is carried out in the liquid (or supercritical or subcritical) phase, it is advantageous to work at a pressure of 1-100 bars and in the presence of one or more solvents. Suitable solvents include any chemical that is a liquid under reaction conditions, including, but not limited to, oxygenated hydrocarbons such as alcohols, ethers, esters, and ketones, aromatic and aliphatic hydrocarbons such as toluene and hexane, nitriles such as acetonitrile, liquid $CO_2$ (in the supercritical or subcritical state), and water. Preferable solvents include water, liquid $CO_2$, and oxygenated hydrocarbons such as alcohols, ethers, esters, ketones, and the like, or mixtures thereof. Preferred oxygenated solvents include lower aliphatic $C_1$-$C_4$ alcohols such as methanol, ethanol, isopropanol, and tert-butanol, or mixtures thereof, and water. Fluorinated alcohols can be used. It is particularly preferable to use mixtures of the cited alcohols with water.

If epoxidation is carried out in the liquid (or supercritical or subcritical) phase, it is advantageous to use a buffer. The buffer will typically be added to the solvent to form a buffer solution. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may range from 3 to 10, preferably from 4 to 9 and more preferably from 5 to 7. Suitable salts of oxyacids contain an anion and cation. The anion portion of the salt may include anions such as phosphate, monohydrogenphosphate, dihydrogenphosphate, sulfate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Examples include $NH_4$, $NBu_4$, $NMe_4$, Li, Na, K, Cs, Mg, and Ca cations. More preferred buffers include alkali metal phosphate and ammonium phosphate buffers. Buffers may preferably contain a combination of more than one suitable salt. Typically, the concentration of buffer in the solvent is from about 0.0001 M to about 1 M, preferably from about 0.001 M to about 0.3 M. The buffer useful in this invention may also include the addition of ammonia gas to the reaction system.

The following examples merely illustrate the invention. Those skilled in the art will recognize many variations that are within the spirit of the invention and scope of the claims.

EXAMPLE 1

Preparation of Pd—Bi—Pb/$TiO_2$, Pd—Bi/$TiO_2$, and Pd—Au/TiO2 Catalysts

Catalyst 1A (Pd—Bi—Pb/$TiO_2$):

Lead nitrate (0.69 g) and an aqueous solution of disodium palladium tetrachloride (1.11 g, 19.7 wt. % Pd) are added to a solution of bismuth nitrate (0.3 g $Bi(NO_3)_3$ dissolved in 15 mL, 2.56 M solution of nitric acid, 16.6% by volume of 70% $HNO_3$) with mixing. The Pd—Bi—Pb solution is then added by incipient wetness to spray dried titania (20 g, 30 micron size, 40 $m^2$/g, calcined in air at 700° C.). The solids are calcined in air in a muffle furnace by heating at 10° C./min to 110° C. for 4 hours and then at 2° C./min to 300° C. for 4 hours. These calcined solids are then washed with an aqueous sodium bicarbonate solution (40 mL, containing 2.25 g $NaHCO_3$), followed by deionized water (40 mL, four times). The washed solids are vacuum dried (20 torr) at 50° C. for 16 hours and then calcined in a muffle furnace by heating at 10° C./min to 110° C. for 4 hours and then heating at 2° C./min to 600° C. for 4 hours. The solids are then transferred to a quartz tube and treated with a 4 vol. % hydrogen in nitrogen stream at 100° C. for 1 hour (100 cc/hr), followed by nitrogen for 30 minutes while cooling from 100° C. to 30° C. to produce Catalyst 1A. Catalyst 1A contains 0.83 wt. % Pd, 0.5 wt. % Bi, 1.6 wt. % Pb, 57 wt. % Ti and less than 100 ppm Na.

Comparative Catalyst 1B (Pd—Au/$TiO_2$):

Aqueous sodium tetrachloro aurate (16.54 g, 19.95 wt. % Au) and aqueous disodium tetrachloro palladate (27.86 g, 19.74 wt. % Pd) are added to 1.2 L of deionized water with swirling in a round-bottom flask. To this solution, sodium bicarbonate (12.5 g) is added as a powder, followed by spray dried $TiO_2$ (500 g, 35 micron average size, 43 $m^2$/g, air calcined at 700° C.). The pH of the slurry is adjusted to 7.3 by adding solid portions of sodium bicarbonate (approximately 100 g is required) and the reaction slurry is agitated by rotation of the flask at 25 rpm at a 45 degree angle for 18 hours at 23° C. The solids are then filtered, washed once with deionized water (1.2 L), and calcined in air in a muffle furnace by heating at 10° C./min to 110° C. for 4 hours and then at 2° C./min to 300° C. for 4 hours. These calcined solids are then washed with deionized water (1.2 L) eight times. The washed solids are calcined in a muffle furnace by heating at 10° C./min to 110° C. for 4 hours and then heating at 2° C./min to 600° C. for 4 hours. The solids are then transferred to a quartz tube and treated with a 4 vol. % hydrogen in nitrogen stream at 100° C. for 1 hour (100 cc/hr), followed by nitrogen for 30 minutes while cooling from 100° C. to 30° C. to produce Comparative Catalyst 1B. Comparative Catalyst 1B contains 1 wt. % Pd. 0.6 wt. % Au, 58 wt. % Ti and less than 20 ppm Cl.

Comparative Catalyst 1C (Pd—Bi/TiO$_2$):

An aqueous solution of disodium palladium tetrachloride (1.11 g, 19.7 wt. % Pd) is added to a solution of bismuth nitrate (0.35 g Bi(NO$_3$)$_3$ dissolved in 15 mL, 2.56 M solution of nitric acid, 16.6% by volume of 70% HNO$_3$). The Pd—Bi solution is then added by incipient wetness to spray dried titania (20 g, 30 micron size, 40 m$^2$/g, calcined in air at 700° C.). The solids are calcined in air in a muffle furnace by heating at 10° C./min to 110° C. for 4 hours and then at 2° C./min to 300° C. for 4 hours. These calcined solids are then washed twice with an aqueous sodium bicarbonate solution (40 mL, containing 0.9 g NaHCO$_3$), followed by deionized water (40 mL, five times). The washed solids are vacuum dried (20 torr) at 50° C. for 16 hours and then calcined in a muffle furnace by heating at 10° C./min to 110° C. for 4 hours and then heating at 2° C./min to 600° C. for 4 hours. The solids are then transferred to a quartz tube and treated with a 4 vol. % hydrogen in nitrogen stream at 100° C. for 1 hour (100 cc/hr), followed by nitrogen for 30 minutes while cooling from 100° C. to 30° C. to produce Catalyst 1C. Catalyst 1C contains 0.94 wt. % Pd, 0.64 wt. % Bi, 58 wt. % Ti and less than 100 ppm Na.

EXAMPLE 2

Epoxidation Reaction Using Catalysts from Example 1

A 300 cc stainless steel reactor is charged with the supported noble metal catalyst (0.07 g of 1A, 1B, or 1C), TS-1 powder (0.63 g), methanol (~100 g), and a buffer solution (13 g of 0.1 M aqueous ammonium phosphate, pH=6). The reactor is then charged to 300 psig with a feed consisting of 2% hydrogen, 4% oxygen, 5% propylene, 0.5% methane and the balance nitrogen (volume %) for runs utilizing a 2:1 O$_2$:H$_2$ ratio or a feed consisting of 4% hydrogen, 4% oxygen, 5% propylene, 0.5% methane and the balance nitrogen (volume %) for runs utilizing a 1:1 O$_2$:H$_2$ ratio. The pressure in the reactor is maintained at 300 psig via a backpressure regulator with the feed gases passed continuously through the reactor at 1600 cc/min (measured at 23° C. and one atmosphere pressure). In order to maintain a constant solvent level in the reactor during the run, the oxygen, nitrogen and propylene feeds are passed through a two-liter stainless steel vessel (saturator) preceding the reactor, containing 1.5 liters of methanol. The reactor is stirred at 1500 rpm. The reaction mixture is heated to 60° C. and the gaseous effluent is analyzed by an online GC every hour and the liquid analyzed by offline GC at the end of the 18 hour run. Propylene oxide and equivalents ("POE"), which include propylene oxide ("PO"), propylene glycol ("PG"), and propylene glycol methyl ethers (PMs), are produced during the reaction, in addition to propane formed by the hydrogenation of propylene.

The epoxidation results (see Table 1) show that a TS-1 and Pd—Bi—Pb/TiO$_2$ mixed catalyst shows a significant increase in propylene selectivity resulting from reduced propane make, compared to TS-1 and Pd—Bi/TiO$_2$ or TS-1 and Pd—Au/TiO$_2$ mixed catalysts.

TABLE 1

Epoxidation Results

| Catalyst | O$_2$:H$_2$ Ratio | Catalyst Productivity[1] | Propylene Selectivity (%)[2] |
|---|---|---|---|
| 1A | 2 | 0.34 | 93 |
| 1A | 1 | 0.57 | 88 |
| 1B* | 2 | 0.39 | 81 |
| 1B* | 1 | 0.7 | 68 |
| 1C* | 2 | 0.45 | 89 |
| 1C* | 1 | 0.41 | 86 |

[1]Productivity = grams POE produced/gram of catalyst per hour.
[2]Propylene Selectivity = 100 − (moles propane/(moles POE + moles propane)) × 100.
*Comparative Example

I claim:

1. A process for producing propylene oxide comprising reacting propylene, hydrogen and oxygen in the presence of a titanium zeolite and a supported catalyst comprising palladium, lead, bismuth, and a carrier.

2. The process of claim 1 wherein the titanium zeolite is a titanium silicalite.

3. The process of claim 1 wherein the supported catalyst contains 0.01 to 10 weight percent palladium, 0.01 to 10 weight percent lead, and 0.001 to 5 weight percent bismuth.

4. The process of claim 1 wherein the carrier is selected from the group consisting of carbon, titania, zirconia, niobia, silica, alumina, silica-alumina, tantalum oxide, molybdenum oxide, tungsten oxide, titania-silica, zirconia-silica, niobia-silica, and mixtures thereof.

5. The process of claim 1 wherein the reaction is performed in the presence of a solvent comprising methanol.

6. The process of claim 5 wherein the reaction is performed in the presence of a buffer.

7. A catalyst comprising palladium, lead, bismuth, and a titanium or vanadium zeolite.

8. The catalyst of claim 7 wherein the titanium or vanadium zeolite is a titanium silicalite.

9. A catalyst mixture comprising a titanium or vanadium zeolite and a supported catalyst comprising palladium, lead, bismuth, and a carrier.

10. The catalyst mixture of claim 9 wherein the titanium zeolite is a titanium silicalite.

11. The catalyst mixture of claim 9 wherein the carrier is selected from the group consisting of carbon, titania, zirconia, niobia, silica, alumina, silica-alumina, tantalum oxide, molybdenum oxide, tungsten oxide, titania-silica, zirconia-silica, niobia-silica, and mixtures thereof.

* * * * *